United States Patent
Ishikawa (10) Patent No.: US 9,462,933 B2
(45) Date of Patent: Oct. 11, 2016

(54) IMAGE PICKUP UNIT FOR ENDOSCOPE

(71) Applicant: OLYMPUS CORPORATION, Tokyo (JP)

(72) Inventor: Shinya Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/881,590

(22) Filed: Oct. 13, 2015

(65) Prior Publication Data

US 2016/0029879 A1 Feb. 4, 2016

Related U.S. Application Data

(63) Continuation of application No. PCT/JP2014/062466, filed on May 9, 2014.

(30) Foreign Application Priority Data

Aug. 5, 2013 (JP) ................................. 2013-162450

(51) Int. Cl.
*A61B 1/05* (2006.01)
*H04N 5/225* (2006.01)
(Continued)

(52) U.S. Cl.
CPC ............... *A61B 1/051* (2013.01); *A61B 1/005* (2013.01); *A61B 1/00114* (2013.01);
(Continued)

(58) Field of Classification Search
CPC .... A61B 1/051; A61B 1/05; A61B 1/00114; A61B 1/00018; G02B 23/2484; H04N 2005/2255; H04N 5/2251; H04N 5/2257
USPC .................................................. 348/76, 340
See application file for complete search history.

(56) References Cited

U.S. PATENT DOCUMENTS 5,220,198 A * 6/1993 Tsuji ........................ A61B 1/05
257/680
6,313,456 B1* 11/2001 Miyashita ......... H01L 27/14618
250/208.1
(Continued)

FOREIGN PATENT DOCUMENTS

EP 2018043 A1 1/2009
JP H04-105634 A 4/1992
(Continued)

OTHER PUBLICATIONS

International Search Report dated Aug. 5, 2014 issued in PCT/JP2014/062466.
(Continued)

*Primary Examiner* — John P Leubecker
(74) *Attorney, Agent, or Firm* — Scully, Scott, Murphy & Presser, PC (57) ABSTRACT

An image pickup unit for an endoscope includes: an image pickup device including a plurality of connection terminal portions arrayed on a back face that is a surface opposite to a light-receiving surface; a planar rigid printed wiring board including a substrate connection portion and an electric cable connection portion; a flexible printed wiring board including a fixation portion connected to the image pickup device and the rigid printed wiring board, an extension portion extending from an outer periphery of the fixation portion, and a flexed portion provided at a boundary between the fixation portion and the extension portion; an electric cable connected to the electric cable connection portion of the rigid printed wiring board; and an electronic component mounted on the extension portion of the flexible printed wiring board.

3 Claims, 7 Drawing Sheets

(51) Int. Cl.
*A61B 1/00* (2006.01)
*G02B 23/24* (2006.01)
*A61B 1/005* (2006.01)

(52) U.S. Cl.
CPC .......... *A61B 1/00124* (2013.01); *G02B 23/24* (2013.01); *H04N 5/225* (2013.01); *H04N 5/2251* (2013.01); *H04N 2005/2255* (2013.01)

(56) References Cited

U.S. PATENT DOCUMENTS

| | | | |
|---|---|---|---|
| 2002/0080233 A1* | 6/2002 | Irion | H04N 5/2251 348/65 |
| 2004/0263680 A1 | 12/2004 | Sonnenschein et al. | |
| 2006/0109368 A1* | 5/2006 | Ayrenschmalz | A61B 1/0011 348/340 |
| 2009/0021618 A1* | 1/2009 | Schwarz | H04N 5/2251 348/294 |
| 2011/0199473 A1 | 8/2011 | Kojima | |
| 2011/0249106 A1* | 10/2011 | Makino | H04N 5/2254 348/76 |
| 2012/0206583 A1* | 8/2012 | Hoshi | A61B 1/042 348/76 |
| 2013/0169777 A1* | 7/2013 | Zen | A61B 1/051 348/76 |
| 2015/0312457 A1* | 10/2015 | Kojima | G02B 23/2484 348/76 |

FOREIGN PATENT DOCUMENTS

| | | |
|---|---|---|
| JP | H05-224135 A | 9/1993 |
| JP | H11-326787 A | 11/1999 |
| JP | 2007-073958 A | 3/2007 |
| JP | 2009-027709 A | 2/2009 |
| JP | 2011-166080 A | 8/2011 |
| JP | 2011-217887 A | 11/2011 |
| JP | 2012-064883 A | 3/2012 |
| WO | WO 2005/002210 A1 | 1/2005 |

OTHER PUBLICATIONS

Japanese Office Action dated Feb. 17, 2015 issued in JP 2014-559007.

* cited by examiner

FIG. 9

IMAGE PICKUP UNIT FOR ENDOSCOPE

CROSS REFERENCE TO RELATED APPLICATION

This application is a continuation application of PCT/JP2014/062466 filed on May 9, 2014 and claims benefit of Japanese Application No. 2013-162450 filed in Japan on Aug. 5, 2013, the entire contents of which are incorporated herein by this reference.

BACKGROUND OF THE INVENTION

1. Field of the Invention

The present invention relates to an image pickup unit for an endoscope, the image pickup unit including an image pickup device including connection terminal portions on a back surface thereof.

2. Description of the Related Art

For observation of a site that is hard to observe such as the inside of a living body or the inside of a structure, an endoscope that can be introduced from the outside to the inside of the living body or the structure and includes an image pickup unit for picking up an optical image is used in, for example, the medical field or the industrial field. An image pickup unit for an endoscope includes an objective lens that forms an image of an object, and an image pickup device disposed on an image-forming surface of the objective lens, which is generally called, e.g., a CCD (charge-coupled device) or a CMOS (complementary metal oxide semiconductor) sensor. There are image pickup devices of the type in which connection terminal portions for electrical connection with a substrate is provided on a back surface on the opposite side of a surface on which light from the image pickup device is incident (light-receiving surface) in order to reduce the mounting area of the substrate. For example, Japanese Patent Application Laid-Open Publication No. 2007-73958 discloses an image pickup device package with connection terminal portions provided on a back surface thereof. Use of such image pickup device including connection terminal portions on a back surface thereof enables mounting area reduction. Where an image pickup device including connection terminal portions on a back surface thereof such as disclosed in Japanese Patent Application Laid-Open Publication No. 2007-73958 is used in an image pickup unit for an endoscope, a form in which the image pickup device is mounted on a flexible printed wiring board, the flexible printed wiring board is flexed so as to extend rearward (direction opposite to an object) along an optical axis and electric cables disposed inside the endoscope are connected to distal end portions of the flexed parts of the flexible printed wiring board may be employed. As described above, flexing a flexible printed wiring board with an image pickup device mounted thereon so as to extend rearward enables reduction in area of projection of an outer shape of the image pickup unit on a planar surface that is perpendicular to an optical axis.

SUMMARY OF THE INVENTION

An image pickup unit for an endoscope according to an aspect of the present invention includes: an image pickup device including a plurality of connection terminal portions arrayed on a back face that is a surface opposite to a light-receiving surface; a planar rigid printed wiring board including a substrate connection portion and an electric cable connection portion; a flexible printed wiring board including a fixation portion connected to the image pickup device and the rigid printed wiring board, an extension portion extending from an outer periphery of the fixation portion, and a flexed portion provided at a boundary between the fixation portion and the extension portion; an electric cable connected to the electric cable connection portion of the rigid printed wiring board; and an electronic component mounted on the extension portion of the flexible printed wiring board, and within an area hidden behind the image pickup device as the image pickup device is viewed from the light-receiving surface side along an axis perpendicular to the light-receiving surface, the connection terminal portions of the image pickup device are connected to a plurality of pads provided on a first surface of the fixation portion of the flexible printed wiring board and the substrate connection portion of the rigid printed wiring board is connected to a second surface that is a back face of the first surface of the fixation portion, the flexible printed wiring board is flexed at the flexed portion so that the extension portion extends in a direction away from the image pickup device, and the electric cable connection portion includes a metal film portion extending along a thickness direction of the rigid printed wiring board, and a guide portion that guides a distal end portion of the electric cable so that the distal end portion is joined to the metal film portion along the direction in which the metal film portion extends.

DETAILED DESCRIPTION OF THE PREFERRED EMBODIMENTS

Preferred embodiments of the present invention will be described below with reference to the drawings. Note that in each of the drawings used for the below description, components are illustrated on difference scales so that the respective components have sizes that are large enough to be recognized in the drawing, and the present invention is not limited only to the counts and amounts, and the shapes of the components, and the size ratios and the relative positional relationships among the components illustrated in the drawings.

First Embodiment

An example of an embodiment of the present invention will be described below. First, an example of a configuration of an endoscope 101 including an image pickup unit 1 for an endoscope according to the present invention will be described with reference to FIG. 1. Note that hereinafter, the image pickup unit 1 for an endoscope is simply referred to as "image pickup unit 1".

Figure 1:
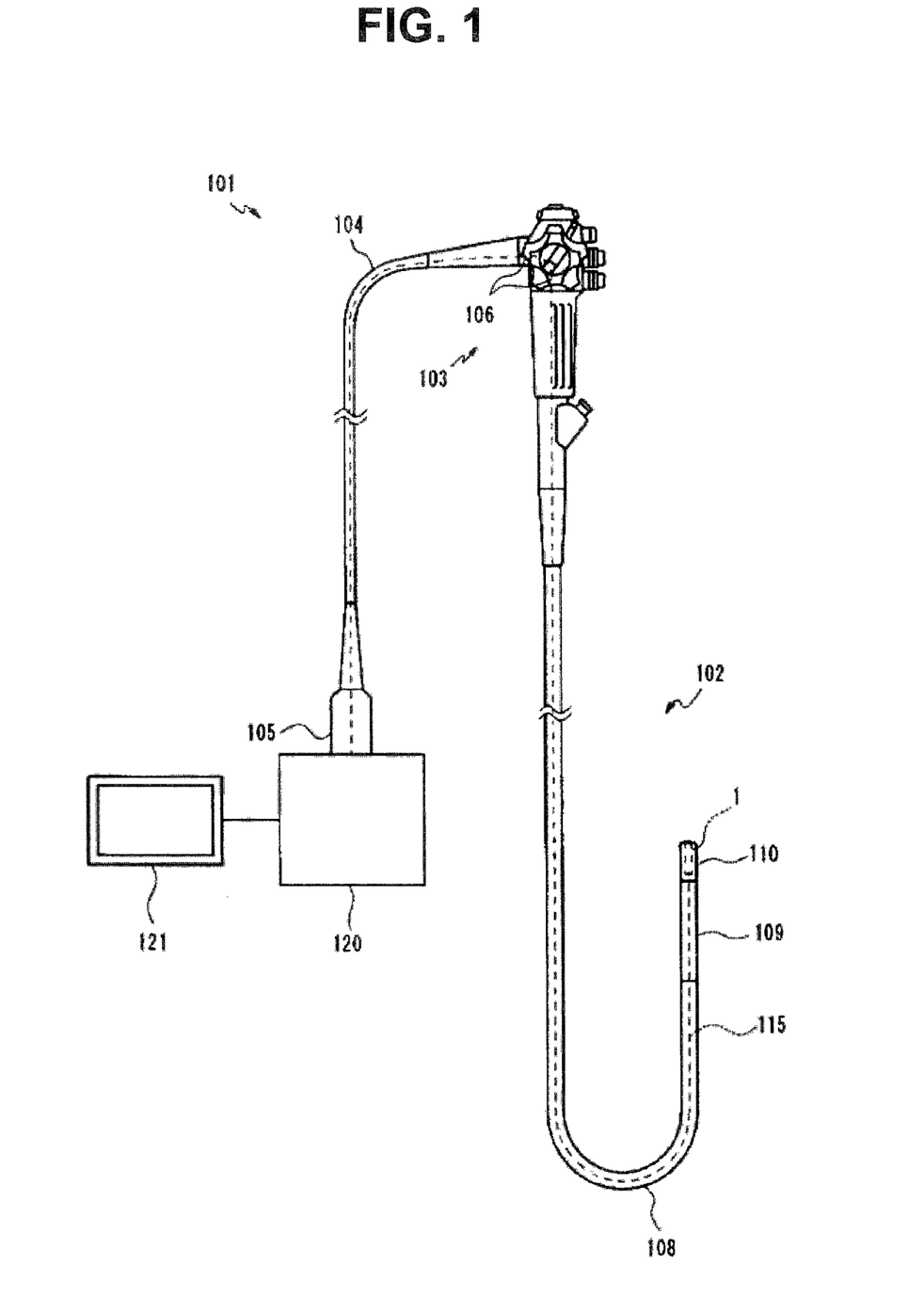
FIG. 1 is a diagram illustrating a configuration of an endoscope.

The endoscope 101 in the present embodiment has a configuration that can be introduced to the inside of a subject such as a human body and optically picks up an image of a predetermined site to be observed inside the subject. Note that the subject or object to which the endoscope 101 is introduced is not limited to a human body, and may be another living body or an artificial object such as a machine or a building.

The endoscope 101 in the present embodiment mainly includes, as an example, an insertion portion 102 to be introduced to the inside of a subject or object, an operation portion 103 positioned at a proximal end of the insertion portion 102, and a universal cord 104 extending from a side portion of the operation portion 103.

The insertion portion 102 includes a distal end portion 110 disposed at a distal end, a bending portion 109 disposed on the proximal end side of the distal end portion 110, the bending portion 109 being to be bent by a remote operation, and a flexible tube portion 108 disposed on the proximal end side of the bending portion 109 and connected to the distal end side of the operation portion 103, the flexible tube portion 108 having flexibility, which are provided consecutively. Note that the endoscope 101 may be what is called a rigid endoscope including no flexible region in an insertion portion thereof. Also, the endoscope 101 may include no bending portion that is to be bent by a remote operation.

In the distal end portion 110, the image pickup unit 1 and an illuminating light output section 113 (not illustrated in FIG. 1) are provided. Also, in the operation portion 103, angle operation knobs 106 for operating bending of the bending portion 109 are provided.

At a proximal end portion of the universal cord 104, an endoscope connector 105 to be connected to an external apparatus 120 is provided. The external apparatus 120 to which the endoscope connector 105 is connected includes, for example, a light source section, an image processing section and an image display section 121.

Also, the endoscope 101 includes electric cables 115 and an optical fiber bundle 114 (not illustrated in FIG. 1) inserted through the universal cord 104, the operation portion 103 and the insertion portion 102.

The electric cables 115 are configured so as to electrically connect the connector portion 105 and the image pickup unit 1. As a result of the connector portion 105 being connected to the external apparatus 120, the image pickup unit 1 is electrically connected to the external apparatus 120 via the electric cables 115. The electric cables 115 allow connection between the external apparatus 120 and a ground (ground potential) of the image pickup unit 1, power supply, and signal input/output between the external apparatus 120 and the image pickup unit 1.

The image processing section provided in the external apparatus 120 includes a configuration that generates a video signal based on an image pickup device output signal outputted from the image pickup unit 1 and outputs the video signal to the image display section 121. In other words, in the present embodiment, an optical image picked up by the image pickup unit 1 is displayed as a video image on the display section 121. Note that the image processing section and the image display section 121 may partly or wholly be disposed in the endoscope 101.

Also, the optical fiber bundle is configured so as to deliver light emitted from the light source section in the external apparatus 120 to the illuminating light output section 113 in the distal end portion 110. Note that the light source section may be disposed in the operation portion 103 or the distal end portion 110 of the endoscope 101.

Figure 2:
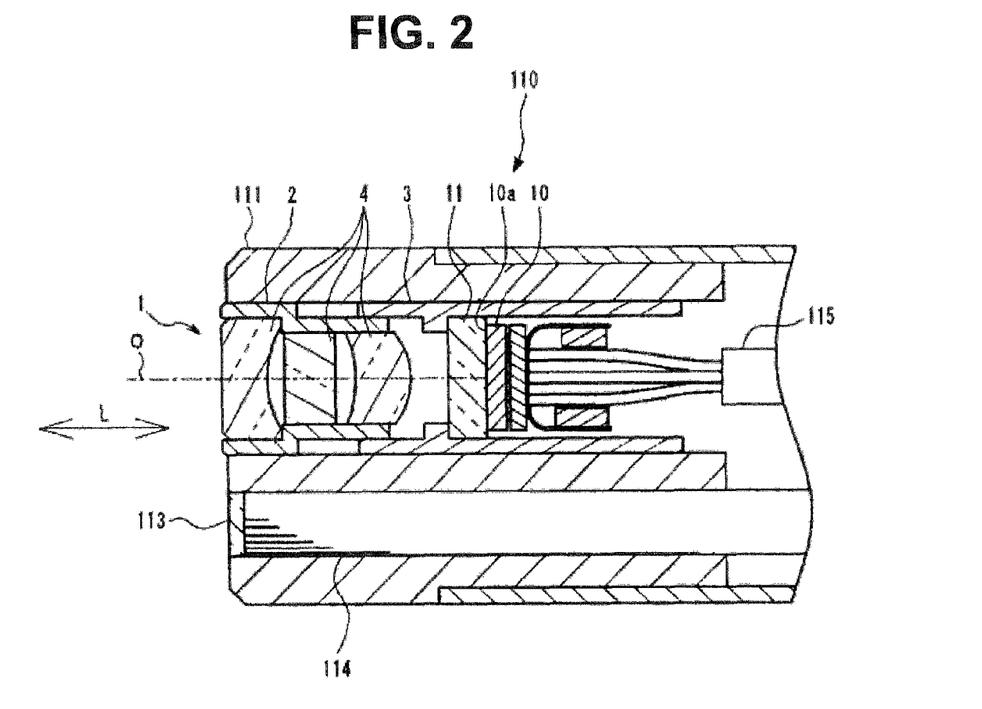
FIG. 2 is a diagram illustrating a configuration of a distal end portion of the endoscope.

Next, a configuration of the distal end portion 110 will be described. As illustrated in FIG. 2, in the distal end portion 110, the image pickup unit 1 and the illuminating light output section 113 are disposed in such a manner that the image pickup unit 1 and the illuminating light output section 113 are fixed to a holding portion 111. The holding portion 111 is a rigid member exposed at a distal end face of the distal end portion 110.

In the present embodiment, as an example, the image pickup unit 1 is disposed so as to pick up an image in a distal end direction along a longitudinal direction (insertion axis direction) of the distal end portion 110, which is indicated by arrow L in FIG. 2. More specifically, the image pickup unit 1 is disposed so that an objective lens 4 described below has an optical axis O along a longitudinal direction of the insertion portion 102. Note that the image pickup unit 1 may be disposed so that the optical axis O forms a predetermined angle with the longitudinal direction of the insertion portion 102.

Also, the illuminating light output section 113 has a configuration that outputs light outputted from the optical fiber bundle 114 so as to illuminate an object for the image pickup unit 1. In the present embodiment, the illuminating light output section 113 is configured so as to output light in the distal end direction from the distal end face of the distal end portion 110 along the longitudinal direction of the insertion portion 102.

The image pickup unit 1 includes the objective lens 4, an image pickup device 10 and electronic components 23. These members included in the image pickup unit 1 are held by a holding frame 3 having a substantially frame shape. In the present embodiment, the holding frame 3 is a cylindrical member surrounding a periphery of the optical axis O.

Note that in the below, a direction from the image pickup unit 1 toward an object (left side in FIG. 2) along the optical axis O of the image pickup unit 1 is referred to as "front side or forward" and a direction opposite to that direction is referred to as "rear side or rearward".

The objective lens 4 includes one or more optical members such as lenses for forming an object image on a light-receiving surface 10a of the image pickup device 10, the optical member(s) being disposed inside a lens barrel 2 having a cylindrical shape. Note that the objective lens 4 may include an optical element such as a reflective mirror, a prism or an optical filter. Also, the objective lens 4 may include a configuration that can change a focal length.

The image pickup device 10 is an image sensor such as a CCD or a CMOS sensor. In the present embodiment, as an example, the image pickup device 10 is fixed to a predetermined position inside the holding frame 3 via protection glass 11, which is a transparent member bonded to the light-receiving surface 10a. The image pickup device 10 is disposed so that the light-receiving surface 10a is substantially perpendicular to the optical axis O.

The image pickup device 10 is electrically connected to distal end portions of the electric cables 115 extending from the image pickup unit 1 to the inside of the endoscope 101 via an electronic circuit section 20, which will be described in detail later. The electric cables 115 are configured so as to electrically connect the image pickup device 10 and an external device. Here, the external device is the connector portion 105 in the present embodiment, but the type of the external device is not specifically limited. For example, if the electric cables 115 that electrically connect the image pickup unit 1 and the connector portion 105 can be divided, the external device is a component such as a connector that allows the division of the electric cables 115. Also, for example, if the endoscope includes, inside, an electronic circuit section including an image processing section, the external device is the electronic circuit section.

In the electronic circuit section 20, one or more electronic components 23 are mounted, and each of the electronic components 23 is electrically connected to at least either the image pickup device 10 or the electric cable 115 via the electronic circuit section 20.

Figure 3:
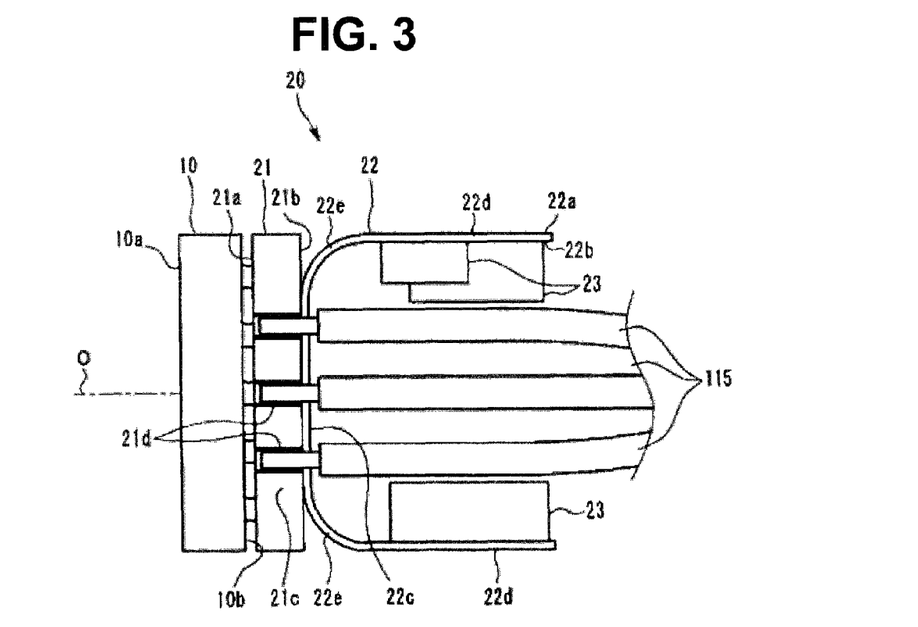
FIG. 3 is a side view of an image pickup device, an electronic circuit section and distal end portions of electric cables.
Figure 4:
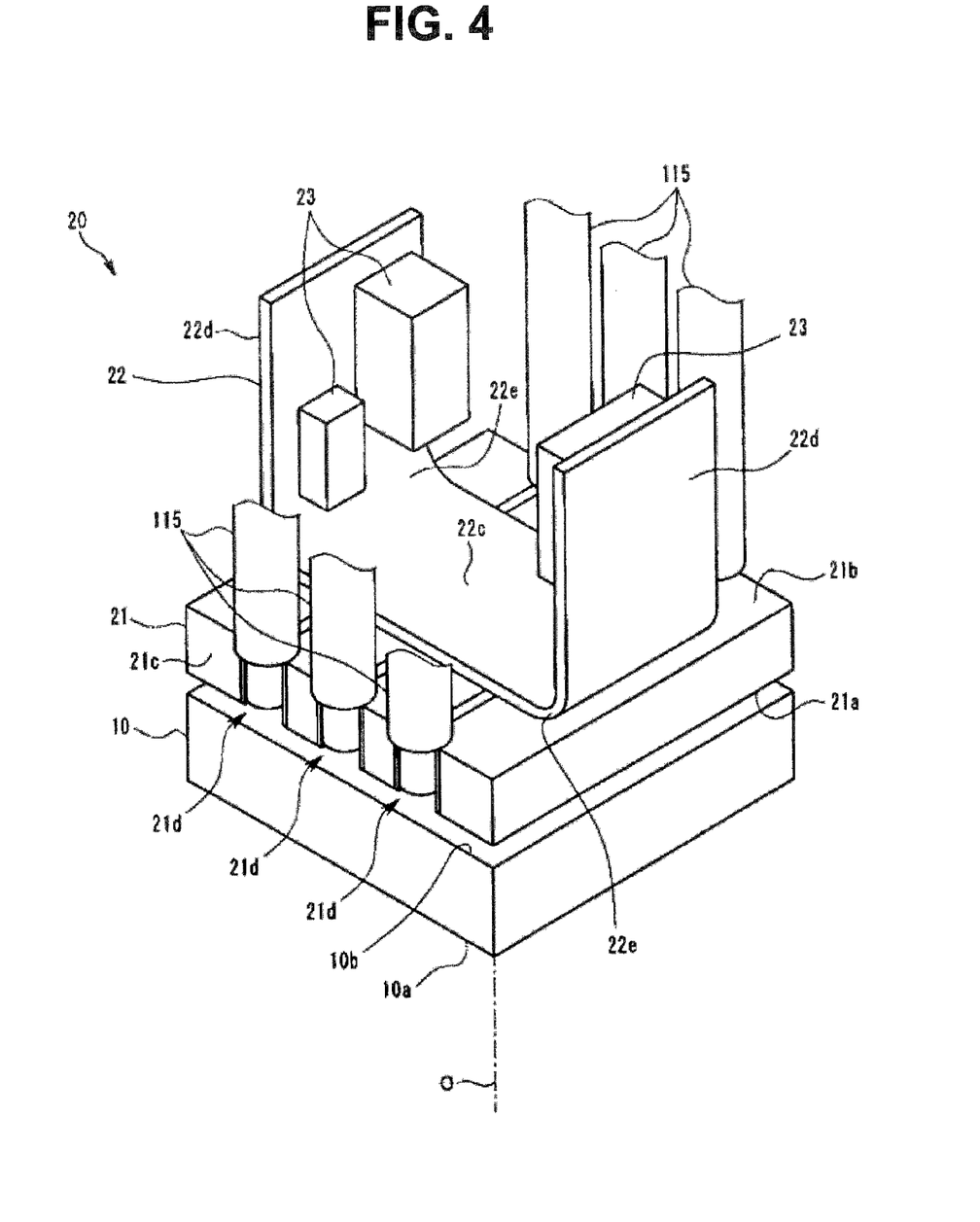
FIG. 4 is a perspective view of the electronic circuit section.
Figure 5:
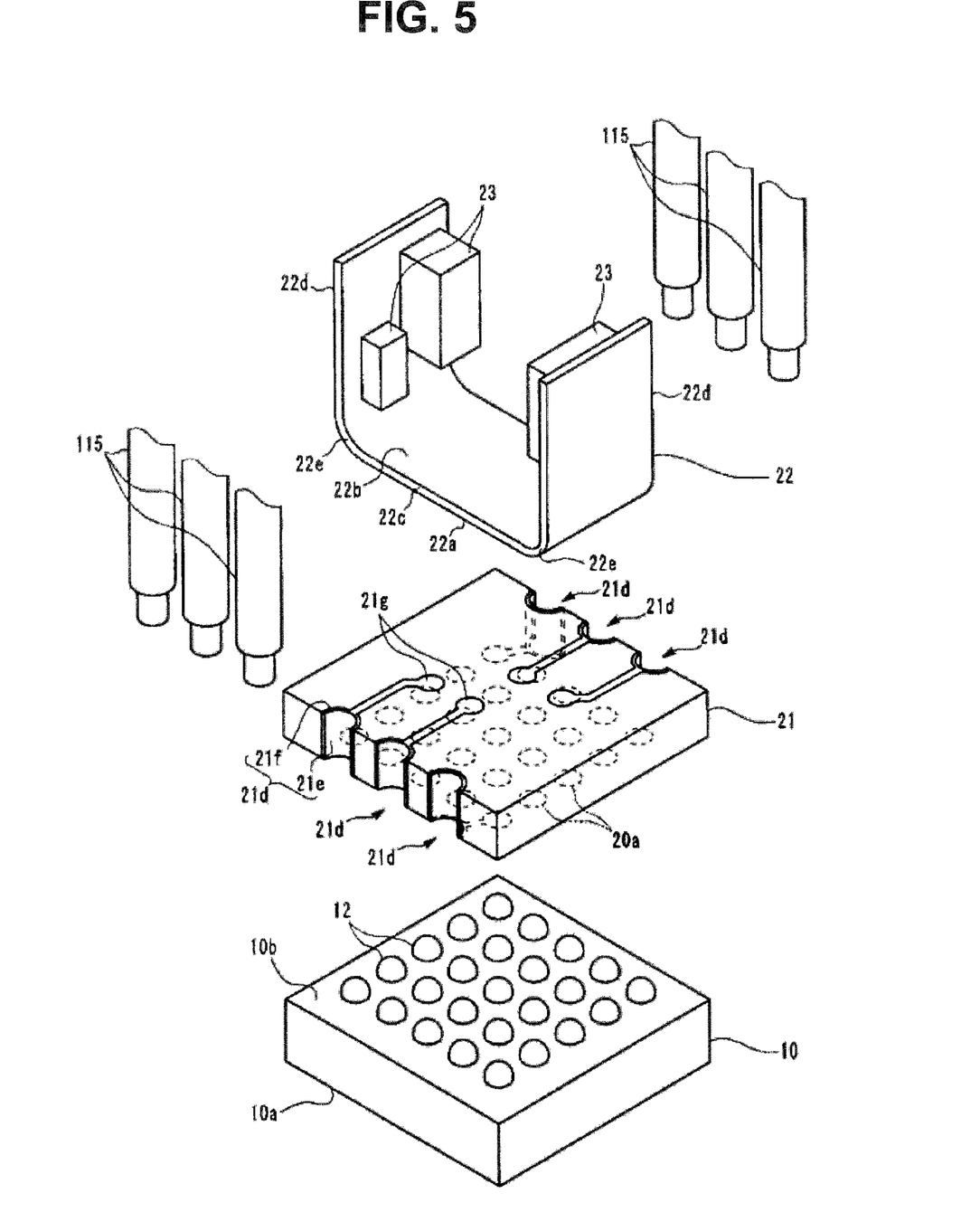
FIG. 5 is an exploded view of the electronic circuit section.

A configuration of the image pickup device 10 and a configuration of the electronic circuit section 20 connecting the image pickup device 10 and the electric cables 115 will be described below. FIG. 3 is a side view of the image pickup device 10, the electronic circuit section 20 and distal end portions of the electric cables 115. FIG. 4 is a perspective view of the image pickup device 10, the electronic circuit section 20 and the distal end portions of the electric cables 115. FIG. 5 is an exploded view of the electronic circuit section.

In the image pickup device 10, a plurality of connection terminal portions 12 each including a conductive material such as a metal are arrayed on a back face 10b that is a surface facing a direction opposite to the light-receiving surface 10a. A surface mount electronic component form in which a plurality of connection terminal portions are arrayed on a predetermined surface of an electronic component like the image pickup device 10 in the present embodiment is generally referred to as "BGA (ball grid array)" or "LGA (land grid array)". The connection terminal portions of the surface mount electronic components such as described above and pads on a circuit substrate are joined to each other by means of a known technique such as metal joining such as solder joining or a conductive adhesive, and thereby electrically connected.

In recent years, using a technique called through-silicon vias (TSVs), a plurality of connection terminal portions can be formed on a back face of a chip (die) including an integrated circuit, the chip being one cut out from a silicon wafer, enabling reduction in mounting area of the chip including the integrated circuit.

The image pickup device 10 used in the image pickup unit 1 for an endoscope according to the present embodiment is a chip-size (die-size) one using such through-silicon vias, and has a size of approximately 3 mm square as viewed in a direction perpendicular to the light-receiving surface 10a.

In the present embodiment, as an example, the image pickup device 10 includes a form called "BGA", and in a state before the image pickup device 10 is mounted, a solder ball, which is a substantially-spherical region of solder, is formed in each of the plurality of connection terminal portions 12.

The image pickup device 10 is mounted in the electronic circuit section 20. The electronic circuit section 20 includes a rigid printed wiring board 21, which is a substantially flat plate-shaped electronic circuit substrate having a predetermined thickness, and a flexible printed wiring board 22, which is a substantially film-shaped electronic circuit substrate having flexibility.

The electronic circuit section 20 includes a plurality of conductive pads 20a to which the plurality of connection terminal portions 12 of the image pickup device 10 are joined. The pads 20a are provided on either the rigid printed wiring board 21 or the flexible printed wiring board 22.

In the present embodiment, as an example, the pads 20a are provided on the rigid printed wiring board 21. In other words, the image pickup device 10 is mounted on the rigid printed wiring board 21. The rigid printed wiring board 21 is a rigid electronic circuit substrate including a conductive layer on each of a first surface 21a and a second surface 21b, which are principal surfaces, and having predetermined stiffness. The rigid printed wiring board 21 may include three or more conductive layers including conductive layer (s) disposed inside.

As illustrated in FIG. 5, the rigid printed wiring board 21 has a substantially-rectangular flat plate shape having a predetermined thickness. The rigid printed wiring board 21 has an outer shape that is substantially the same as that of the image pickup device 10 as viewed from a direction along the optical axis O.

The connection terminal portions 12 of the image pickup device 10 are joined to the pads 20a formed on the first surface 21a, which is one of the principal surfaces of the rigid printed wiring board 21. In other words, the first surface 21a of the rigid printed wiring board 21 is substantially parallel to the light-receiving surface 10a of the image pickup device 10, and is a surface facing a direction that is the same as a direction the light-receiving surface 10a faces (the front side of the image pickup unit 1). As a result of the image pickup device 10 being mounted on the rigid printed wiring board 21 having predetermined stiffness, reliability of connection between the connection terminal portions 12 of the image pickup device 10 and the pads 20a can be enhanced.

In the rigid printed wiring board 21, cable connection portions 21d to which the distal end portions of the electric cables 115 are joined are formed. The cable connection portions 21d are configured so as to, when the electric cables 115 are joined to the cable connection portions 21d, electrically connect an electronic circuit formed on the rigid printed wiring board 21 and the electric cables 115. Also, when the electric cables 115 are joined to the cable connection portions 21d, the distal end portions of the electric cables 115 are substantially perpendicular to the second surface 21b of the rigid printed wiring board 21, and the electric cables 115 extend in a direction opposite to the first surface 21a (rearward in the image pickup unit 1) from the joining parts.

More specifically, each cable connection portion 21d includes a metal film portion 21f extending along a thickness direction of the rigid printed wiring board 21, and a guide portion 21e that guides the distal end portion of the corresponding electric cable 115 so that the distal end portion of the electric cable 115 is joined to the metal film portion 21f along the direction in which the metal film portion 21f extends.

The guide portion 21e is, for example, a groove or hole region provided along the thickness direction of the rigid printed wiring board, the groove or hole region allowing the distal end portion of the electric cable 115 to be fitted therein.

The metal film portion 21f is electrically connected to the electronic circuit formed on the rigid printed wiring board 21. The metal film portion 21f has a length that is substantially the same as the thickness of the rigid printed wiring board 21 in the thickness direction of the rigid printed wiring board 21.

In the present embodiment, as an example, as illustrated in FIG. 5, the cable connection portions 21d are formed at side face portions 21c of the rigid printed wiring board 21. Each cable connection portion 21d includes a groove-shaped guide portion 21e provided through the entirety in the thickness direction of the rigid printed wiring board 21 along a direction substantially perpendicular to the second surface 21b, that is, along the thickness direction of the rigid printed wiring board 21 at the corresponding side face portion 21c, and a metal film portion 21f disposed so as to cover an entire inner face of the guide portion 21e and extending in the thickness direction of the rigid printed wiring board 21.

Note that in the illustrated present embodiment, each cable connection portion 21d is a groove portion having a substantially-semicircular cross-sectional shape, but each cable connection portion 21d may be a groove portion having a substantially V or substantially-rectangular cross-sectional shape.

The electric cables 115 are soldered to the metal film portions 21f in the groove-shaped guide portions 21e with the electric cables 115 placed along the direction in which the guide portions 21e extend. As described above, the guide portions 21e operate to position the electric cables 115 relative to the rigid printed wiring board 21 in soldering work, thereby facilitating the work, and to determine placement of the distal end portions of the electric cables 115 relative to the rigid printed wiring board 21 after the soldering (joining). Here, the placement of the distal end portions of the electric cables 115 relative to the rigid printed wiring board 21 means, as described above, a state in which the distal end portions of the electric cables 115 are substantially perpendicular to the second surface 21b and the electric cables 115 extend rearward from the rigid printed wiring board 21.

As a result of the electric cables 115 being soldered to the metal film portions 21f of the cable connection portions 21d, the electric cables 115 are electrically connected to the electronic circuit formed on the rigid printed wiring board 21. In this state, the electric cables 115 are electrically connected to the image pickup device 10 mounted on the rigid printed wiring board 21.

As a result of the groove-shaped guide portions 21e that open outward being provided at the side face portions 21c of the rigid printed wiring board 21 and the metal film portions 21f to which the electric cables 115 are soldered being provided on respective inner surfaces of the guide portions 21e like the present embodiment, a soldering iron can easily be applied during soldering work, enabling facilitation of work of soldering the distal end portions of the electric cables 115 to the metal film portions 21f.

Although the arrangement of the electric cable connection portions 21d is not specifically limited, in the present embodiment, as illustrated in the Figures, a plurality of electric cable connection portions 21d are formed at a pair of side faces that are parallel to each other from among four side faces of the substantially rectangular rigid printed wiring board 21. Also, the number of electric cable connection portions 21d is arbitrarily determined according to the number of electric cables 115 necessary for driving the image pickup device 10.

Also, on the rigid printed wiring board 21, substrate connection portions 21g for electrically connecting the electronic circuit formed on the rigid printed wiring board 21 and an electronic circuit formed on the later-described flexible printed wiring board 22 are formed.

In the present embodiment, the substrate connection portions 21g are metal pads provided on the second surface 21b of the rigid printed wiring board 21. The substrate connection portions 21g are electrically connected to the electronic circuit formed on the rigid printed wiring board 21.

The flexible printed wiring board 22 is a film-like electronic circuit substrate having flexibility. Such electronic circuit substrate having flexibility is generally called, e.g., "FPC (flexible printed circuit) substrate". Since a basic structure of the flexible printed wiring board 22 is a known technique, detailed description thereof will be omitted. The flexible printed wiring board 22 includes a conductive layer on each of a first surface 22a and a second surface 22b, which are principal surfaces. Note that the flexible printed wiring board 22 may include three or more conductive layers.

The flexible printed wiring board 22, which is located behind the image pickup device 10, includes a fixation portion 22c, which is a region to be stacked on the rigid printed wiring board 21 in a thickness direction, extension portions 22d, which are regions extending from the fixation portion 22c, and flexed portions 22e, which are regions resulting from the flexible printed wiring board 22 being flexed along respective boundaries between the fixation portion 22c and the extension portions 22d.

The fixation portion 22c is a region disposed so that the thickness direction thereof is substantially parallel to the optical axis O in the image pickup unit 1. In other words, the fixation portion 22c is disposed so that the principal surfaces are substantially perpendicular to the optical axis O in the image pickup unit 1.

Hereinafter, from among the pair of principal surfaces of the flexible printed wiring board 22, a principal surface that faces the front side of the image pickup unit 1 in the fixation portion 22c is defined as a first surface 22a. In other words, the first surface 22a of the flexible printed wiring board 22 is a surface that is substantially parallel to the light-receiving surface 10a of the image pickup device 10 within the fixation portion 22c and faces a direction that is the same as a direction the light-receiving surface 10a faces (the front side of the image pickup unit 1).

The fixation portion 22c is fixed on the first surface 21a or the second surface 21b of the rigid printed wiring board 21 within an area hidden behind the image pickup device 10 as the image pickup unit 1 is viewed from the front side along the optical axis O. Here, since the thickness directions of the rigid printed wiring board 21 and the fixation portion 22c correspond to each other, the rigid printed wiring board 21 and the fixation portion 22c are stacked on each other in the thickness direction. There is no specific limitation on a method for fixing the fixation portion 22c to the rigid printed wiring board 21, and, e.g., an adhesive or a two-sided adhesive tape may be used.

Also, in the fixation portion 22c, substrate connection portions (not illustrated) configured so as to, when the fixation portion 22c is fixed to the rigid printed wiring board 21, electrically connect the substrate connection portions 21g provided on the rigid printed wiring board 21 and the electronic circuit provided on the flexible printed wiring board 22 are formed. A form of the electrical connection between the substrate connection portions 21g on the rigid printed wiring board 21 and the substrate connection portions on the flexible printed wiring board 22 are not specifically limited, and, for example, a conductive adhesive, a conductive adhesive film or solder joining may be employed. Also, the connection between the substrate connection portions 21g on the rigid printed wiring board 21 and the substrate connection portions on the flexible printed wiring board 22 may be established by mechanical direct contact between contacts provided in both portions.

As a result of the fixation portion 22c being fixed to the rigid printed wiring board 21, the electronic circuit formed on the flexible printed wiring board 22 and the electronic circuit formed on the rigid printed wiring board 21 are electrically connected. Note that, where a conductive adhesive, a conductive adhesive film or solder joining is employed, the electrical connection between the rigid printed wiring board 21 and the flexible printed wiring board 22 and the mechanical fixation and electrical connection between the rigid printed wiring board 21 and the flexible printed wiring board 22 can be provided by same means.

In the present embodiment, as an example, the fixation portion 22c is fixed on the second surface 21b, which is a surface of the rigid printed wiring board 21 that faces rearward. In other words, the rigid printed wiring board 21 and the fixation portion 22c are stacked on each other in such a manner that the second surface 22b of the rigid printed wiring board 21 and the first surface 22a of the flexible printed wiring board 22 face each other.

Also, in the present embodiment, the fixation portion 22c has a substantially-rectangular shape that is smaller than that of the rigid printed wiring board 22, and is disposed so that outer sides thereof are substantially parallel to outer sides of the rigid printed wiring board 21. Note that the fixation portion 22d may have another polygonal shape such as a substantially-triangular shape or a substantially-hexagonal shape.

Each extension portion 22d is a region that extends from an outer peripheral portion of the fixation portion 22c and is not fixed to the rigid printed wiring board 21. At a boundary portion between the extension portion 22d and the fixation portion 22c, a flexed portion 22e resulting from the flexible printed wiring board 22 being flexed is formed.

The flexed portion 22e is a region resulting from the flexible printed wiring board 22 being flexed with the second surface 22b inside. As a result of the flexed portion 22e being formed in the flexible printed wiring board 22, the extension portion 22d extends rearward in the image pickup unit 1 from the fixation portion 22c.

The extension portions 22d are provided at respective positions in the outer peripheral portions of the fixation portion 22c where when the fixation portion 22c is fixed to the rigid printed wiring board 21 and the flexed portions 22e are formed, the extension portions 22d do not interfere with the electric cables 115. Such arrangement enables prevention of interference between the electric cables 115, and the extension portions 22d and the electronic components 23.

Note that the rigid printed wiring board 21 may include one extension portion 22d or a plurality of extension portions 22d. Also, an angle (inner angle) formed by the fixation portion 22c and each extension portion 22d at the relevant flexed portion 22e is not specifically limited, and may be an acute angle, a right angle or an obtuse angle.

The electronic components 23 are mounted on the extension portions 22d. The electronic components 23 are electrically connected to the electronic circuit formed on the flexible printed wiring board 22. Examples of the electronic components 23 include, e.g., a driver IC, a capacitor and a resistance, and those required for driving the image pickup device 10 are arbitrarily disposed. The types and number of the electronic components 23 included in the electronic circuit section 20 are not specifically limited.

As a result of the fixation portion 22c being fixed to the rigid printed wiring board 21, the electronic components 23 are electrically connected to the image pickup device 10 and the electric cables 115.

In the present embodiment, as an example, the flexible printed wiring board 22 includes two extension portions 22d. The two extension portions 22d extend from a pair of outer sides parallel to each other from among the four outer sides of the fixation portion 22c having a substantially-rectangular shape, in a direction substantially perpendicular to the outer sides. Here, the outer sides of the fixation portion 22c at which the extension portions 22d are provided are sides along the outer sides of the rigid printed wiring board 21 at which the cable connection portions 21d are not provided when the fixation portion 22c is fixed to the rigid printed wiring board 21.

Also, in the present embodiment, the angle (inner angle) formed by the fixation portion 22c and each extension portion 22d at the relevant flexed portion 22e is a substantially-right angle. Therefore, as a result of the flexed portions 22e being formed in the flexible printed wiring board 22, two extension portions 22d extends on the rear side of the image pickup unit 1 in substantially parallel to each other.

Therefore, in the present embodiment, as the image pickup unit 1 is viewed from the front along the optical axis O, the pair of extension portions 22d are disposed substantially perpendicular to the outer sides of the rigid printed wiring board 21 at which the cable connection portions 21d are arranged. The electronic components 23 are mounted on parts of the second surface 22b that are surfaces of the pair of substantially-parallel extension portions 22d facing each other. Therefore, as the image pickup unit 1 is viewed from the front side, the pair of extension portions 22d and the electronic components 23 are hidden behind the image pickup device 10.

As described above, in the image pickup unit 1 according to the present embodiment, the image pickup device 10 is mounted on the rigid printed wiring board 21, and the electronic components 23 are mounted on the extension portions 22d of the flexible printed wiring board 22 fixed to the rigid printed wiring board 21. Then, as the image pickup unit 1 is viewed from the front side, the rigid printed wiring board 21 has an outer shape hidden behind the image pickup device 10. Also, the flexible printed wiring board 22 and the electronic components 23 are disposed so as to be hidden behind the image pickup device 10 as the image pickup unit 1 is viewed from the front side.

Also, the electric cables 115 are joined to the cable connection portions 21d of the rigid printed wiring board 21 so that the respective distal end portions extend rearward along the thickness direction of the rigid printed wiring board 21.

Here, in general, in order to obtain strength of joining electric cables to pads on a printed wiring board, it is necessary to secure the area of the joining surface that has a predetermined value or more. Thus, for example, where a plurality of electric cables are soldered to a plurality of pads provided on a principal surface of a printed wiring board, the area of the joining surface cannot be increased unless distal end portions of the electric cables are soldered to the pads with the distal end portions laid substantially parallel to the principal surface of the printed wiring board.

On the other hand, in the present embodiment, if the image pickup device 10 has a size of approximately 3 mm square, the rigid printed wiring board 21 also has a size of approximately 3 mm square. When a plurality of pads are provided to join a plurality of electric cables to a printed wiring board that is small in area, the small pads are densely placed at narrow intervals, resulting in high difficulty in soldering work. Also, since distal end portions of the electric cables extend in a direction along principal surfaces of the printed wiring board, it is necessary to provide a space for arranging the electric cables on the outer side relative to an outer periphery of the printed wiring board, which hinders reduction in diameter of the image pickup unit.

However, in the present embodiment, the configuration in which the distal end portions of the electric cables 115 are joined to the cable connection portion 21d along the thickness direction of the rigid printed wiring board 21 enables the electric cables 115 to be arranged so as to be hidden behind the rigid printed wiring board 21 as the image pickup unit 1 is viewed from the front side along the optical axis O. In other words, in the present embodiment, the distal end portions of the electric cables 115 can be disposed so as not to project on the outer side relative to the outer shape of the image pickup device 10 as the image pickup unit 1 is viewed from the front side along the optical axis O.

Also, in the present embodiment, joining parts between the metal film portions 21f and the distal end portions of the electric cables 115 are widened in the thickness direction of the rigid printed wiring board 21, enabling securement of a joining area required for obtainment of strength of joining between both that has a predetermined value or more. This leads to reduction in proportion of the cable connection portions 21d in the area of a principal surface of the rigid printed wiring board 21 and thus contributes to reduction in size of the rigid printed wiring board 21.

As described above, in the image pickup unit 1 according to the present embodiment, the rigid printed wiring board 21, the flexible printed wiring board 22, the electronic components 23 and the distal end portions of the electric cables 115 can be arranged within the area substantially covered by the outer shape of the image pickup device 10 as the image pickup device 10 is viewed in the direction perpendicular to the light-receiving surface 10a, enabling reduction in diameter of the image pickup unit 1.

Also, as with the conventional techniques, when a flexible printed wiring board with an image pickup device mounted thereon is made to extend on the rear side of the image pickup device and electronic components are mounted on and electric cables are further connected to the extension portions, the extension portions need to be long in back in order to obtain an area required for mounting the electronic components and the electric cables.

As opposed to the conventional techniques, in the present embodiment, only the electronic components 23 are mounted on and the distal end portions of the electric cables 115 are not joined to the extension portions 22d of the flexible printed wiring board 22. As described above, the distal end portions of the electric cables 115 are joined to the rigid printed wiring board 21.

Therefore, the area of each extension portion 22d of the flexible printed wiring board 22 can be made to be small compared to those of the conventional techniques. In other words, in the image pickup unit 1 according to the present embodiment, the length of each extension portion 22d of the flexible printed wiring board 22 that extends behind the image pickup device 10 can be reduced, enabling downsizing of the image pickup unit 1 in the optical axis direction.

Also, as in the present embodiment, provision of a plurality of extension portions 22d enables reduction in extension length of each extension portion 22d without decrease in area of the extension portion 22d that allows electronic components 23 to be mounted thereon and also enables downsizing of the image pickup unit 1 in the optical axis direction.

As described above, the image pickup unit 1 for an endoscope according to the present embodiment enables diameter reduction and downsizing in the optical axis direction while the area of the substrate required for mounting the electronic components 23 is secured.

Figure 6:
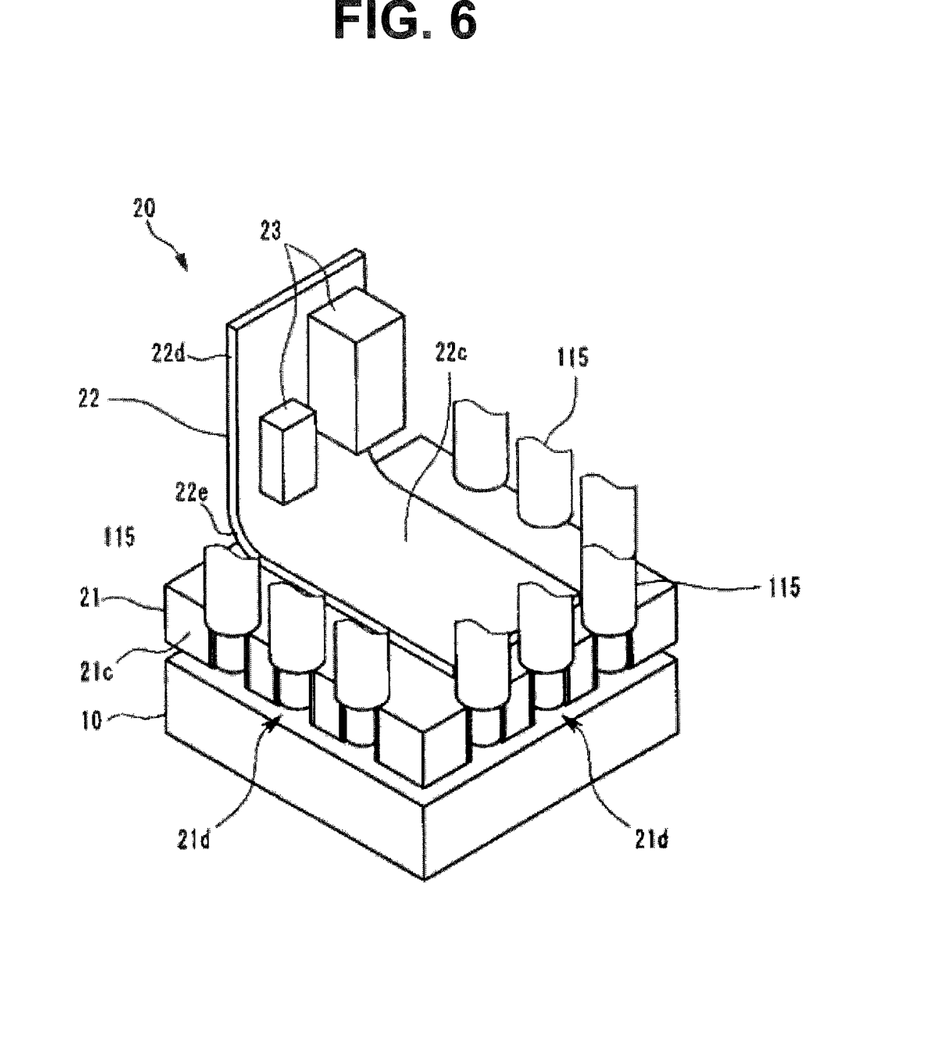
FIG. 6 is a diagram illustrating a first modification of cable connection portions.

Note that although in the above-described embodiment, the flexible printed wiring board 22 includes two extension portions 22d, as in a first modification, which is illustrated in FIG. 6, the flexible printed wiring board 22 may include one extension portion 22d. In the modification illustrated in FIG. 6, cable connection portions 21d are provided at three side face portions 21c of a substantially-rectangular rigid printed wiring board 21.

Figure 7:
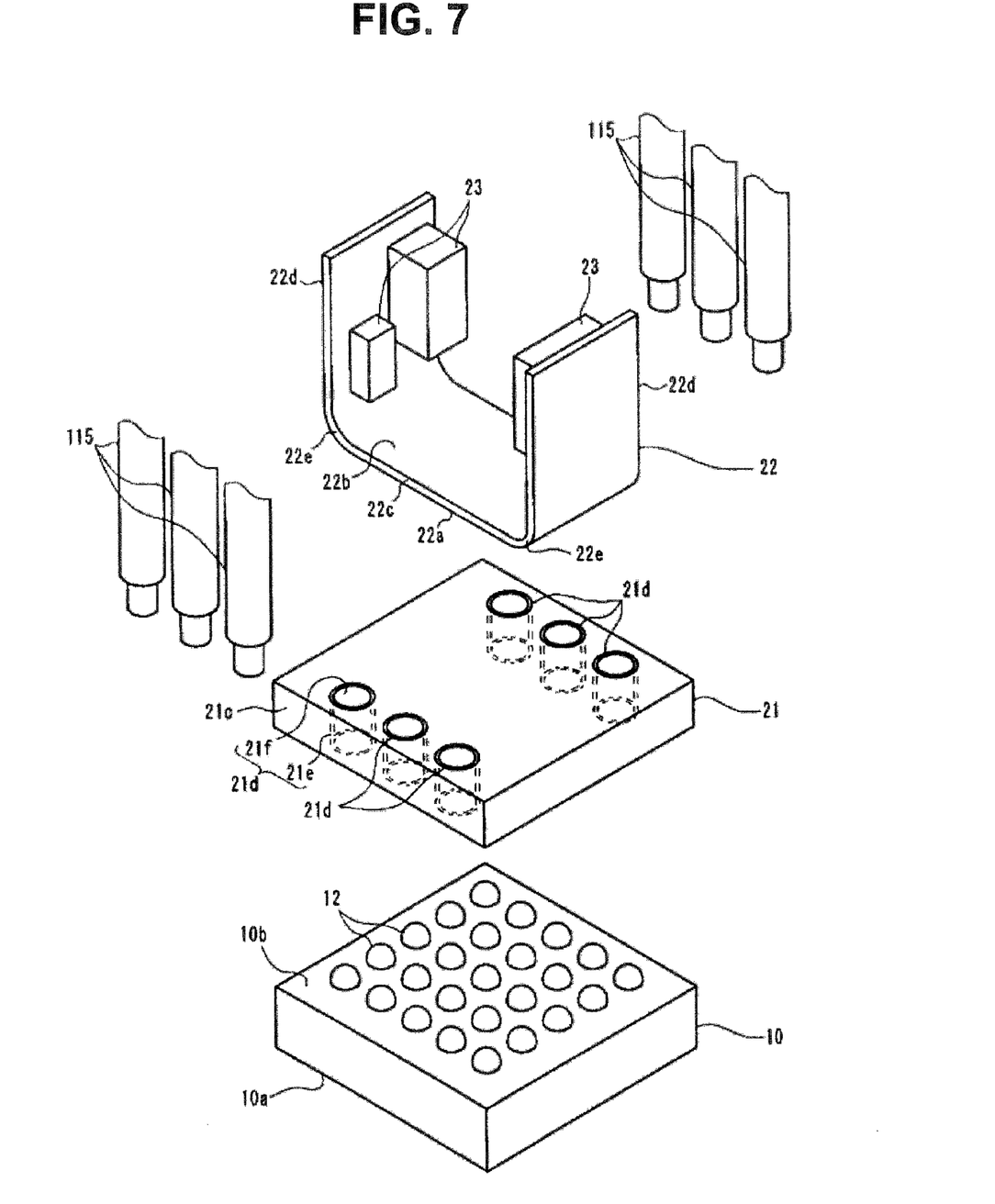
FIG. 7 is a diagram illustrating a second modification of the cable connection portions.

Also, although in the above-described embodiment, the cable connection portions 21d of the rigid printed wiring board 21 are disposed at the side face portions 21c of the rigid printed wiring board 21, the cable connection portions 21d may be disposed at portions of the rigid printed wiring board 21 other than the side face portions 21c. For example, as in a second modification, which is illustrated in FIG. 7, it is possible that cable connection portions 21d do not open outward at side face portions 21c of a rigid printed wiring board 21, but include guide portions 21e each having a hole shape extending through the rigid printed wiring board 21 in a thickness direction and metal film portions 21f provided on respective inner surfaces of the guide portions 21e.

Figure 8:
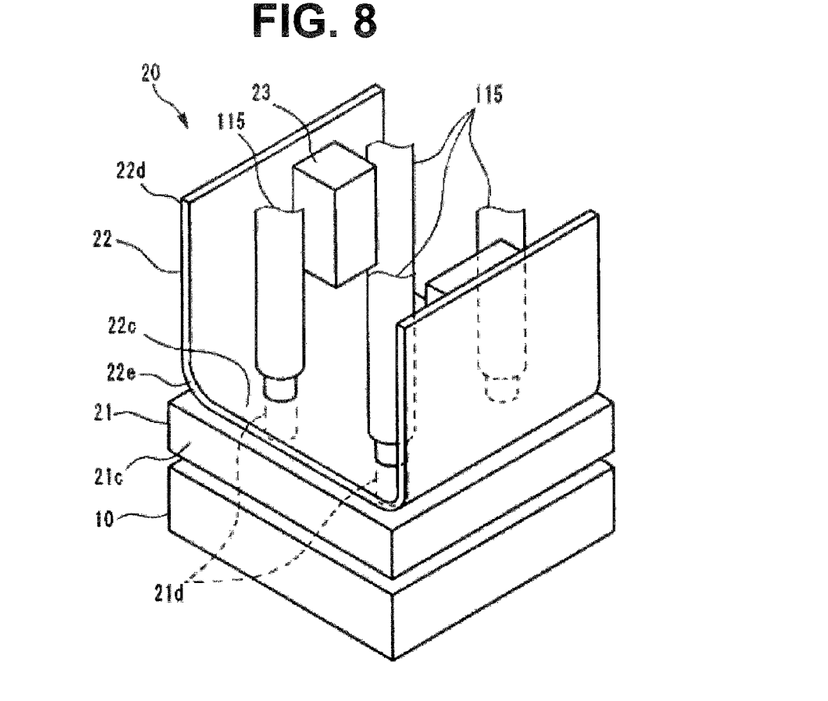
FIG. 8 is a diagram illustrating a third modification of the cable connection portions.

Also, where cable connection portions 21d are formed by guide portions 21e each having a through hole shape and metal film portions 21f, as in a third modification, which is illustrated in FIG. 8, distal end portions of electric cables 115 may be disposed so as to extend through a fixation portion 22c of a flexible printed wiring board 22. As in this modification, where distal end portions of electric cables 115 are made to extend through a fixation portion 22c of a flexible printed wiring board 22, for example, if the distal end portions of the electric cables 115 are arranged close to flexed portions 22e, the distal end portions can be regarded as starting points of flexure of the flexible printed wiring board 22 in a process of forming the flexed portions 22e.

Also, as in the third modification, if distal end portions of a plurality of electric cables 115 are arranged on the inner side relative to the flexed portions 22e, the plurality of electric cables 115 can be arranged more close to one another than that of the embodiment described above, enabling a position where the plurality of electric cable 115 are collected into a bundle to be close to the distal end portions. In other words, if a plurality of electric cables 115 can be collected into a bundle at a more forward position in the image pickup unit 1, the image pickup unit 1 can be shortened in an optical axis direction.

Second Embodiment

Next, a second embodiment of the present invention will be described. The below description will be provided only in terms of differences from the first embodiment, components that are similar to those of the first embodiment will be provided with reference numerals that are the same as those of the first embodiment, and description thereof will arbitrarily be omitted.

Figure 9:
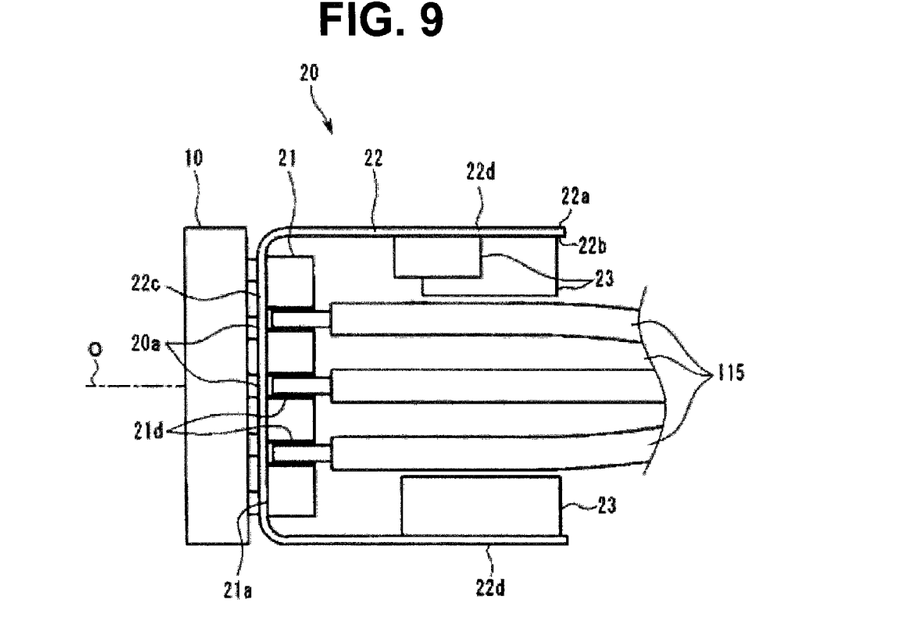
FIG. 9 is a side view of an image pickup device, an electronic circuit section and distal end portions of electric cables in a second embodiment.

The present embodiment is different from the first embodiment in that an image pickup device 10 is mounted on a flexible printed wiring board 22. In other words, although in the first embodiment, the image pickup device 10, the rigid printed wiring board 21 and the flexible printed wiring board 22 are arranged in this order from the front side of the image pickup unit 1, in the present embodiment, the image pickup device 10, the flexible printed wiring board 22 and a rigid printed wiring board 21 are arranged in this order.

More specifically, as illustrated in FIG. 9, in the present embodiment, a plurality of pads 20a are formed on a first surface 22a of a fixation portion 22c of a flexible printed wiring board 22. Also, a first surface 21a of a rigid printed wiring board 21 is fixed on a second surface 22b that is a principal surface on the opposite side of the principal surface of the fixation portion 22c on which the pads 20a are formed.

Although not illustrated here, in each of the second surface 22b of the fixation portion 22c and the first surface 21a of the rigid printed wiring board 21, substrate connection portions for establishing electrical connection between the flexible printed wiring board 22 and the rigid printed wiring board 21 are provided.

The present embodiment as described above also enables diameter reduction and downsizing in an optical direction of an image pickup unit 1 for an endoscope while an area of the substrate required for mounting electronic components 23 is secured as in the above-described first embodiment. In the present embodiment, the first or second modification of the first embodiment described above can be applied also to cable connection portion 22d.

The present invention is not limited to the above-described embodiments and the embodiments can arbitrarily be altered without departing from the spirit and idea of the invention that can be read from the claims and the entire description, and an image pickup unit for an endoscope that involves such alteration also fall within the technical scope of the present invention.

What is claimed is:

1. An image pickup unit for an endoscope, the image pickup unit comprising:
    an image pickup device including a plurality of connection terminal portions arrayed on a back face that is a surface opposite to a light-receiving surface;
    a planar rigid printed wiring board including a substrate connection portion and an electric cable connection portion;
    a flexible printed wiring board including a fixation portion connected to the image pickup device and the rigid printed wiring board, an extension portion extending from an outer periphery of the fixation portion, and a flexed portion provided at a boundary between the fixation portion and the extension portion;
    an electric cable connected to the electric cable connection portion of the rigid printed wiring board; and
    an electronic component mounted on the extension portion of the flexible printed wiring board, wherein:
    within an area hidden behind the image pickup device as the image pickup device is viewed from the light-receiving surface side along an axis perpendicular to the light-receiving surface, the connection terminal portions of the image pickup device are connected to a plurality of pads provided on a first surface of the fixation portion of the flexible printed wiring board and the substrate connection portion of the rigid printed wiring board is connected to a second surface that is a back face of the first surface of the fixation portion;
    the flexible printed wiring board is flexed at the flexed portion so that the extension portion extends in a direction away from the image pickup device; and
    the electric cable connection portion includes a metal film portion extending along a thickness direction of the rigid printed wiring board, and a guide portion that guides a distal end portion of the electric cable so that the distal end portion is joined to the metal film portion along the direction in which the metal film portion extends.

2. The image pickup unit for an endoscope according to claim 1, wherein:
    the guide portion is a groove portion extending in the thickness direction of the rigid printed wiring board at a side face portion of the rigid printed wiring board; and
    the metal film portion is disposed on an inner face of the groove portion.

3. The image pickup unit for an endoscope according to claim 2, wherein the extension portion is disposed at a position where the extension portion and the electronic component mounted on the extension portion do not interfere with the electric cable.

* * * * *